US00PP35928P2

(12) United States Plant Patent
Kolster et al.

(10) Patent No.: US PP35,928 P2
(45) Date of Patent: Jul. 2, 2024

(54) ***HYDRANGEA* PLANT NAMED 'HOKOMASOMA'**

(50) Latin Name: *Hydrangea macrophylla*
Varietal Denomination: Hokomasoma

(71) Applicants: Kolster Holding B.V., Boskoop (NL); Horteve Breeding B.V., Aalsmeer (NL)

(72) Inventors: Peter Rudolf Kolster, Boskoop (NL); Cornelis Pieter Eveleens, Aalsmeer (NL)

(73) Assignees: KOLSTER HOLDING BV, Boskoop (NL), PART INTEREST; HORTEVE BREEDING BV, Aalsmeer (NL), PART INTEREST ( * ) Notice: Subject to any disclaimer, the term of this patent is extended or adjusted under 35 U.S.C. 154(b) by 0 days.

(21) Appl. No.: 18/499,504

(22) Filed: Nov. 1, 2023

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea macrophylla* plant named 'Hokomasoma' that is characterized by its mounded and compact growth habit, its inflorescences that are pink in color, its well-branched habit, and its suitability as a potted plant and garden plant.

3 Drawing Sheets

Botanical classification: *Hydrangea macrophylla.*
Varietal denomination: 'Hokomasoma'.

BACKGROUND OF THE INVENTION

The present invention relates to a new and distinct cultivar of *Hydrangea macrophylla* and will be referred to hereafter by its cultivar name, 'Hokomasoma'. 'Hokomasoma' represents a new bigleaf *Hydrangea*, a perennial shrub grown for use in the landscape, as a potted plant, and as a cut flower.

'Hokomasoma' derived from an ongoing controlled breeding program directed by the Inventors. The goal of the breeding program included developing a new cultivar of *Hydrangea* with good branching, inflorescences with different shades of pink and suitability as a potted plant and as a garden plant.

'Hokomasoma' arose from a controlled cross made by the Inventors in Boskoop, The Netherlands in May of 2014 between an unnamed and unpatented proprietary plant in the Inventor's breeding program, reference no. 12-065-13, as the female parent and *Hydrangea* 'Magical Opal' (U.S. Plant Pat. No. 20,483) as the male parent.

Asexual propagation of the new cultivar was first accomplished by stem cuttings under the direction of the Inventors in July of 2016 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomasoma' as a unique cultivar of *Hydrangea macrophylla.*

1. 'Hokomasoma' exhibits a mounded and compact growth habit.
2. 'Hokomasoma' exhibits inflorescences that are pink in color.
3. 'Hokomasoma' exhibits a well-branched habit.
4. 'Hokomasoma' exhibits suitability as a potted plant and garden plant.

The female parent of 'Hokomasoma' differs from 'Hokomasoma' in having sterile sepals that are picotee in form, longer stems, and leaves that are darker green in color. The male parent of 'Hokomasoma' differs from 'Hokomasoma' in having longer stems, larger leaves, and inflorescences with more flowers that are darker pink in color. 'Hokomasoma' can be most closely compared to the *Hydrangea macrophylla* cultivars 'Kolmagimar' (not patented) and 'Hokomarore' (U.S. Plant Pat. No. 31,264). Both 'Kolmagimar' and 'Hokomarore' are similar to 'Hokomasoma' in having pink inflorescences and suitability as a potted plant. 'Kolmagimar' differs from 'Hokomasoma' in having inflorescences that are slightly darker pink in color, leaf margins that are more dentated, and flower margins that are serrate. 'Hokomarore' differs from 'Hokomasoma' in having sterile flowers that are more cup-shaped, inflorescence texture that is harder (firmer), and inflorescences with more flowers.

BRIEF DESCRIPTION OF THE DRAWINGS

The accompanying color photographs illustrate the overall appearance and distinct characteristics of the new *Hydrangea*. The photographs were taken of a 1-year-old plant as grown in 2-gallon containers in Abbotsford, British Columbia, Canada.

The photograph in FIG. 1 provides a side view of 'Hokomasoma' in bloom.

Figure 1:
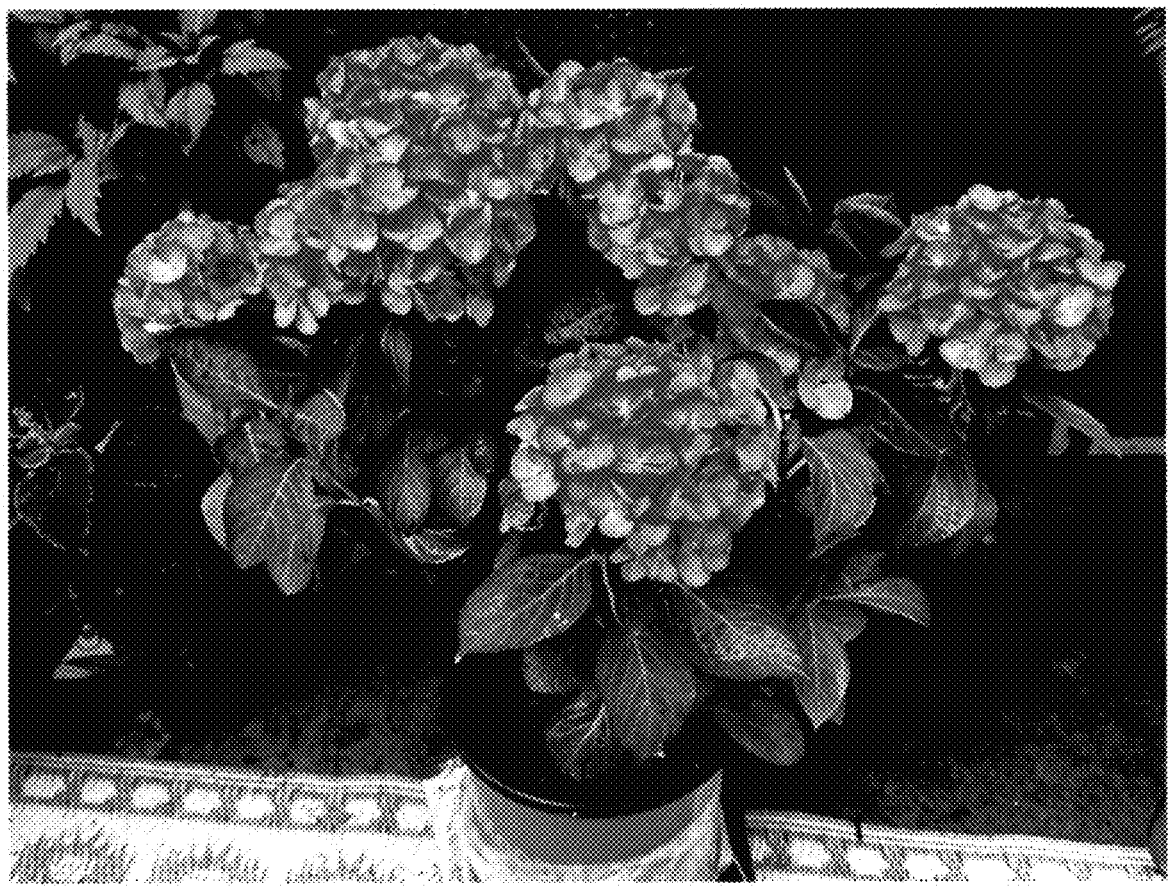
Figure 2:
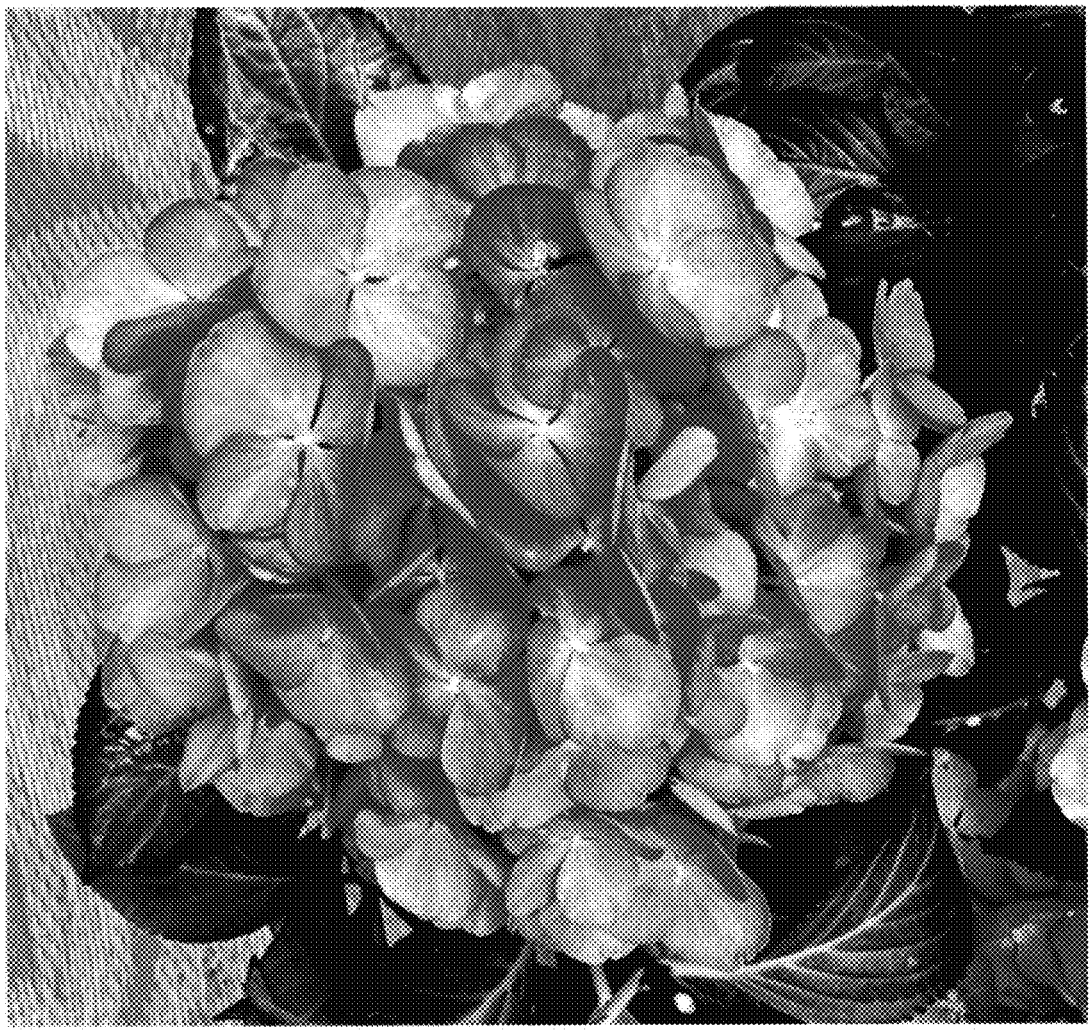

The photograph in FIG. 2 provides a close-up view of an inflorescence of 'Hokomasoma'.

Figure 3:
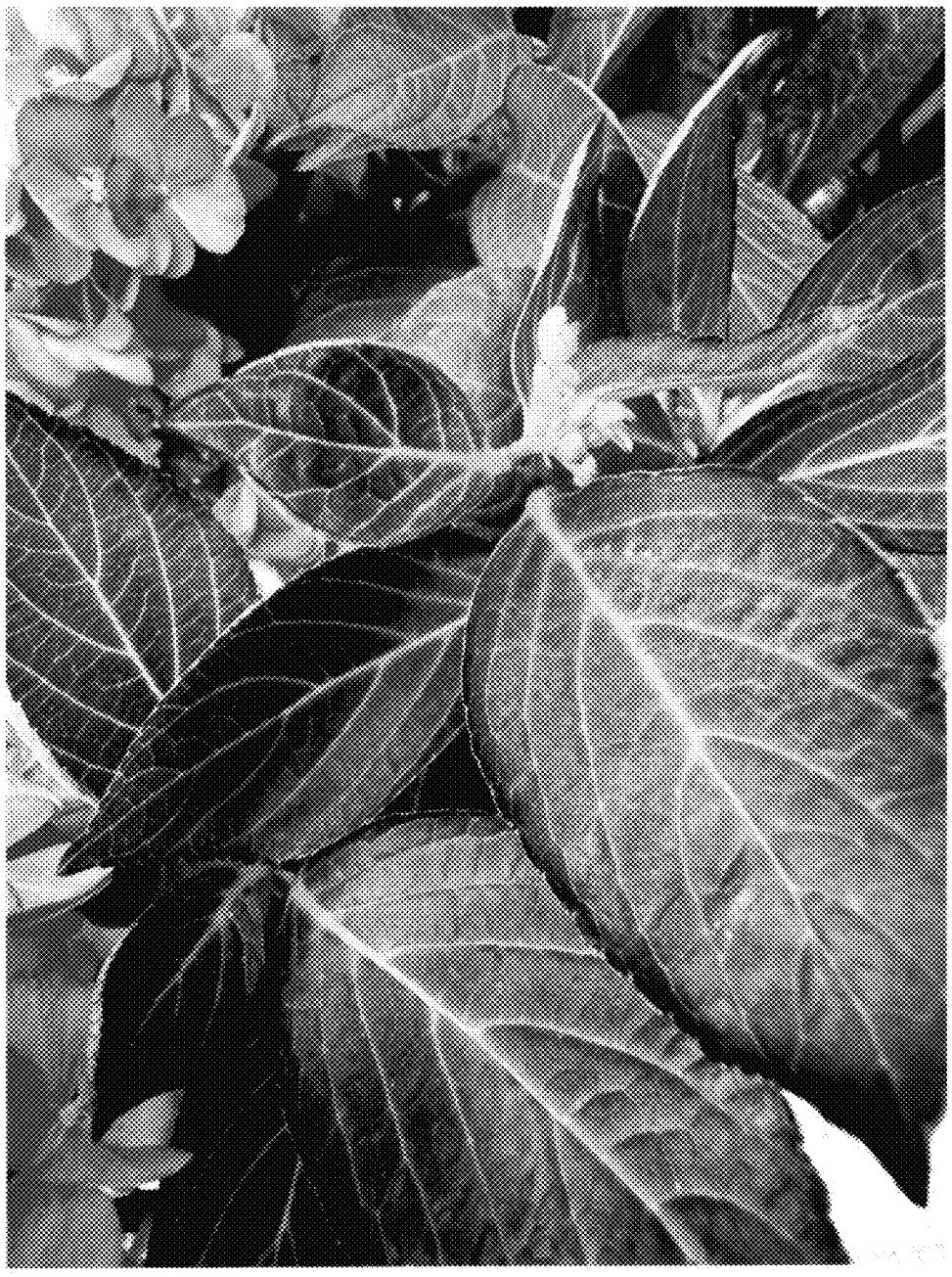

The photograph in FIG. 3 provides a close-up view of the foliage of 'Hokomasoma'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a description of 1-year-old plants as grown outdoors in 2-gallon containers in Abbotsford, British Columbia, Canada. The plants were grown under non-bluing conditions. The phenotype of the new cultivar may vary with variations in environmental, climatic, and cultural conditions, as it has not been tested under all possible environmental conditions. The color determination is in accordance with The 2015 Colour Chart of the Royal Horticultural Society, London, England, except where general color terms of ordinary dictionary significance are used.

General description:

*Blooming period.*—Early summer to autumn in The Netherlands with flowers showy at least for 2 months.

*Plant type.*—Deciduous shrub, mophead type *Hydrangea.*

*Plant habit.*—Compact, upright, rounded.

*Height and spread.*—Reaches 55 cm in in height and 73 cm in width as a 1-year-old plant in a container, reaches 1 m in height and width as a 3-year-old plant in the landscape.

*Hardiness.*—At least in U.S.D.A. Zones 5 to 9.

*Diseases and pests.*—No susceptibility and resistance to diseases or pests has been observed.

*Root description.*—Fine and fibrous, 165A and NN155C in color.

*Propagation.*—Stem cuttings.

*Root development.*—An average of 6 weeks for root initiation with a young rooted plant produced in an average of 18 weeks.

*Growth rate and vigor.*—Moderate.

Branch description:

*Branch shape.*—Round to slightly flattened oval.

*Branch strength.*—Main; strong, lateral; strong and bendable.

*Branch color.*—Young and mature; 144B in color, flushed at the base with 200A, moderately covered in narrow lenticels, 1 mm in length, 202A in color, woody branches; N199A and 200B.

*Branch size.*—Main branches; an average of 27 cm in length, 1 cm in diameter, lateral branches; average of 26 cm in length and 9 mm in diameter.

*Branch surface.*—Young and mature; very glossy, glabrous, older branches; woody, rugose, matte, dry.

*Branch aspect.*—Upright to slightly outward.

*Internode length.*—An average of 5 cm.

*Branching.*—8 main branches, up to 4 lateral branches per main branch.

Foliage description:

*Leaf shape.*—Ovate.

*Leaf arrangement.*—Opposite.

*Leaf division.*—Simple.

*Leaf base.*—Acute.

*Leaf apex.*—Acuminate.

*Leaf margins.*—Serrate.

*Leaf venation.*—Pinnate, upper and lower color 145C.

*Leaf size.*—Up to 13 cm in length and 8 cm in width.

*Leaf attachment.*—Petiolate.

*Leaf number.*—An average of 16 per lateral stem.

*Leaf surface.*—Young and mature; both surfaces glabrous, lower surface matte, upper surface leathery with a slight sheen.

*Leaf color.*—Young; upper surface 138A, lower surface 138B, mature; upper surface 138A, flushed with 139A, margins flushed with 202A, lower surface 138B.

*Petioles.*—An average of 1.5 cm in length and 4 mm in width, both surfaces are glabrous and glossy, 145B in color, lower petioles become slightly flushed with 64A.

Inflorescence description:

*Inflorescence type.*—Terminal panicle, rounded mophead comprised of a sterile flowers above fertile flowers.

*Lastingness of inflorescence.*—Sterile flowers; persistent for an average of 6 weeks, fertile flowers; self-cleaning, an average of 5 days.

*Inflorescence number.*—One per lateral stem.

*Inflorescence size.*—An average of 9 cm in height and 13 cm in diameter.

*Flower number.*—Per mophead; an average of 55 sterile flowers and 10 fertile flowers.

*Flower fragrance.*—None.

*Flower aspect.*—Upright to slightly nodding.

*Flower size.*—Sterile flowers; an average of 4 cm in diameter and 1 cm in depth, fertile flowers; an average of 6 mm in diameter and 4 mm in depth.

*Flower type.*—Rotate.

*Peduncles.*—Strong, bendable, oval in shape, an average of 2 cm in length and 3 mm in diameter, glossy, glabrous, color: young and mature 145A, flushed at the base with 187B, moderately covered in narrow lenticels, 1.5 mm in length, 187B in color.

*Pedicels.*—Sterile flowers; moderately strong, bendable, oval in shape, an average of 2.5 cm in length and 2 mm in diameter, slightly glossy and satiny surface, color; young 193A, mature 65D, flushed with NN155D, fertile flowers; moderately strong, bendable, oval in shape, an average of 1 cm in length and 1 mm in diameter, slightly glossy and satiny surface, color; young 193A, mature 65D, flushed with NN155D.

*Petals.*—Sterile flowers: petal spot (flower bud); 1 mm in depth, 2 mm in diameter, round in shape, color; when young 145C, center 77A, mature NN155D, center 77A, when petals open; are 4 mm in length, 2 mm in width, narrow in shape, cuneate base, acute apex, both surfaces velvety, glabrous and matte, color; both surfaces 73D, fertile flowers: petal spot (flower bud); 4 mm in diameter, 3 mm in depth, round in shape, color; when young 145C, center 77A, mature NN155D, center 77A, when petals open; cup-shaped, 5 mm in length, 3 mm in width, acute apex, both surfaces glabrous and velvety, NN155D, flushed in the center with N75A, petals drop shortly after opening.

*Sepals.*—Sterile flowers; 4, occasionally 5, rotate and slightly overlapping, apex slightly emarginate to obtuse, base is squared, margins are slightly undulate, deltoid and slightly cup-shaped, an average of 2 cm in length and width (at the widest point), both surfaces glabrous, velvety and matte, medium thickness, color: when opening upper and lower surface; 145A to 145B, margins 71B, as it matures turning to NN155A, margins 71B flushed with 62C, when sepals are fully open upper and lower surface; 62A and 62C, flushed with 63B, and changing to 159A, flushed with 68A and 70B, fertile flowers; 5, fused base, apex is acute, an average of 1 mm in length and width (at the widest point), both surfaces glabrous, NN155D in color.

Reproductive organs:

*Gynoecium*.—Sterile flowers; 1 pistil, an average of 1 mm in length, stigma; rounded, NN155D in color, style; 0.4 mm in length, NN155D in color, ovary is superior, 1 mm in depth and diameter, N155A in color, fertile flowers; 2 pistils, an average of 3 mm in length, stigma; club-shaped, 155A in color, style; 1 mm in length, 155A in color, ovary is superior, 1.5 mm in depth, 1 mm in diameter, N155A in color.

*Androecium*.—Sterile flowers; an average of 6 stamens, filaments; an average of 2 mm in length, 0.5 mm in diameter, and NN155D in color, anthers; round in shape, bifid, an average of 1 mm in width, 0.5 mm in depth, NN155D in color, fading to 202A, pollen; low in quantity, 158A in color, fertile flowers; an average of 6 stamens, filaments; an average of 5 mm in length, 0.4 mm in diameter, and NN155D in color, anthers; oval in shape, bifid, an average of 1 mm in width, 1 mm in depth, 155A in color, fading to 202A, pollen; low in quantity, 155A in color.

*Fruit and seed*.—None observed to date.

It is claimed:

1. A new and distinct cultivar of *Hydrangea* plant named 'Hokomasoma' substantially as herein illustrated and described.

* * * * *